United States Patent [19]

Kunne et al.

[11] 3,991,317

[45] Nov. 9, 1976

[54] X-RAY EXAMINING APPARATUS

[75] Inventors: Kurt Kunne; Alfred Hahn; Georg Vogel; Heinz Wons, all of Erlangen, Germany

[73] Assignee: Siemens Aktiengesellschaft, Berlin & Munich, Germany

[22] Filed: Feb. 3, 1976

[21] Appl. No.: 654,736

Related U.S. Application Data

[63] Continuation-in-part of Ser. No. 485,755, July 3, 1974, abandoned.

[30] Foreign Application Priority Data

July 5, 1973 Germany............................ 2334250

[52] U.S. Cl. ............................ 250/445 R; 250/468; 250/523
[51] Int. Cl.² ......................................... G03B 41/16
[58] Field of Search ........... 250/439, 444, 445, 446, 250/447, 448, 449, 522, 523, 525, 468

[56] References Cited
UNITED STATES PATENTS 3,670,163   6/1972   Lajus ................................. 250/447

FOREIGN PATENTS OR APPLICATIONS 1,112,808   8/1961   Germany ........................... 250/447

*Primary Examiner*—Craig E. Church

[57] ABSTRACT

An X-ray examining apparatus having X-ray exposure installation, an inclinable support bed for a patient, and an overhead X-ray tube which is connected with the X-ray exposure installation. The X-ray exposure installation together with the X-ray tube is rotatably supported about a horizontal axis, and the patient support bed for the patient longitudinally slidably carried on the X-ray exposure installation. In this manner, the X-ray tube together with its high voltage cable, and the X-ray exposure installation, are commonly supported at a location which is fixed with respect to the horizontal direction. The X-ray exposure installation may be fastened to a carrier or support tube which envelops the horizontal axis. The carrier tube may be supported, so as to rotate about the horizontal axis, on a carriage which is slidable in a vertical direction along a separating wall.

7 Claims, 4 Drawing Figures

X-RAY EXAMINING APPARATUS

This application is a continuation-in-part application Ser. No. 985,755, filed July 3, 1974, now abandoned.

FIELD OF THE INVENTION

The present invention relates to an X-ray examining apparatus having X-ray exposure installation, an inclinable support bed for a patient, and an overhead X-ray tube which is connected with the X-ray exposure installation.

DISCUSSION OF THE PRIOR ART

An X-ray examining apparatus having an inclinable or tiltable support bed for a patient, an X-ray exposure installation adapted to be moved along the patient support bed, and an overhead X-ray tube which is connected with the patient support bed, is known from German Published Patent Specification 1,541,124. In this X-ray examining apparatus, which has been designed for remote control operation, the X-ray exposure installation which may contain a voluminous X-ray image amplifier with respectively an associated moving picture and television camera, is located at the rearward side of the support bed away from the patient. The foregoing renders the exposure of the patient much easier while enhancing their freedom of movement during the examination. Furthermore, the feeling of reclining patients that they may conceivably be crushed by the large X-ray exposure installation, is avoided. A further advantage of such X-ray examining apparatus lies in the relatively minute radiation imparted to the operating personnel in view of the remote control operability of the apparatus. Unfortunately, the foregoing advantage is partly negated due to the need for frequently entering the examining room for the purpose of changing the X-ray film. In the foregoing, as well as in other X-ray examining apparatus with inclinable patient support bed, it has been found to be disadvantageous in that access to the patient is prevented along one side length of the patient support bed is closed due to the pedestal, and because of the support for the X-ray tube which is movable along the support bed, as well as due to their supply cables.

SUMMARY OF THE INVENTION

Accordingly, it is an object of the present invention to provide a novel X-ray examining apparatus with an overhead X-ray tube which is of simplified construction, without being restricted in its applicability. If possible, conditions may also be created for an improved access to the patient.

In an X-ray examining apparatus pursuant to the above-mentioned type with an X-ray exposure installation which is known per se for taking radiographs on X-ray films and for intensifying the image of an incorporated fluorescent screen for transmitting it to a television camera, together with the X-ray tube is, in an inventive manner, rotably supported about a horizontal axis, and the patient support bed for the patient longitudinally slidably carried on the X-ray exposure installation. In this manner, the X-ray tube together with its high voltage cable, and the X-ray exposure installation, are commonly supported at a location which is fixed with respect to the horizontal direction, so as to obviate the need for guide rails for the X-ray tube support on this side of the patient support bed. Consequently, with the exception of the region of the horizontal axis, also the second side length of the patient support bed thus becomes readily accessible. The partial immobilizing of the X-ray exposure installation does not only simplify the construction of the X-ray examining apparatus by reducing the number of support locations and guides, but also improves the accessibility to the patient. As is further illustrated, the partial immobilizing of the exposure installation is also a necessary precondition in order to more extensively rationalize the operative sequence at the X-ray examining apparatus.

In a particularly advantageous further development of the invention, the X-ray exposure installation may be fastened to a carrier or support tube which envelops the horizontal axis. Such a support tube is particularly suitable for the support of that type of X-ray exposure installation due to its large degree of stiffness symmetrical to the longitudinal axis. In consequence thereof, a carrier or support tube holds out the optically and technologically most advantageous path following the horizontal axis about which the X-ray exposure installation is rotatable, for connections of the most varied type.

A particularly advantageous support for the X-ray examining apparatus is attained when the carrier tube is supported, so as to be rotatable about the horizontal axis, on a carriage which is slidable in a vertical direction along a separating wall. The vertical or height adjustability is required in order to allow the patient support bed, upon tilting of the X-ray examining apparatus in one of two directions for more than 30° from the horizontal, to be lowerable in the horizontal position into the optimum operative height of approximately 70 to 80 cm above the floor. By supporting the carrier tube on a separating wall, not only is there avoided the need for a complex stand which extends into the space below the X-ray examining apparatus so as to allow for a completely unobstructed floor, but concurrently the room in which the X-ray examining apparatus is located is separated into an examining room and a further radiation-screened adjoining room which contains the various connections or cables and auxiliary apparatus. Furthermore, this construction permits a rigid connection between X-ray tube base, X-ray exposure installation and carrier tube, which is of particular advantage for extending the cables through the carrier tube. The conducting of the collective cables through the carrier tube into the adjoining room leads to a considerably enhanced visual appearance of the X-ray examining apparatus.

The accessibility to the patient may be improved to an extraordinary degree when the patient support bed is supported at a distance of 0.5 to 2.0 mm in parallel to the separating wall. Together with the longitudinally displaceable support of the patients support bed on the X-ray exposure installation, this arrangement leads to a construction providing an all-sided access to the patient.

The operative sequences during the examination of the patient, and during the removal of the exposed film material may be readily separated from each other, when the exposed film material is removed from the X-ray exposure installation through the carrier tube. In X-ray exposure installations in which the carrier tube for the X-ray exposure installation is mounted on a separating wall forming a divider for an examining room and an adjoining room, the examining room need no longer be entered for effecting the removal of exposed film material. This will provide a reduction in radiation exposure to personnel charged with the removal of the exposed film material.

BRIEF DESCRIPTION OF THE DRAWINGS

Further details of the invention may now be ascertained from the following description of an exemplary embodiment thereof, taken in conjunction with the accompanying drawings; in which.

DETAILED DESCRIPTION

Figure 1:
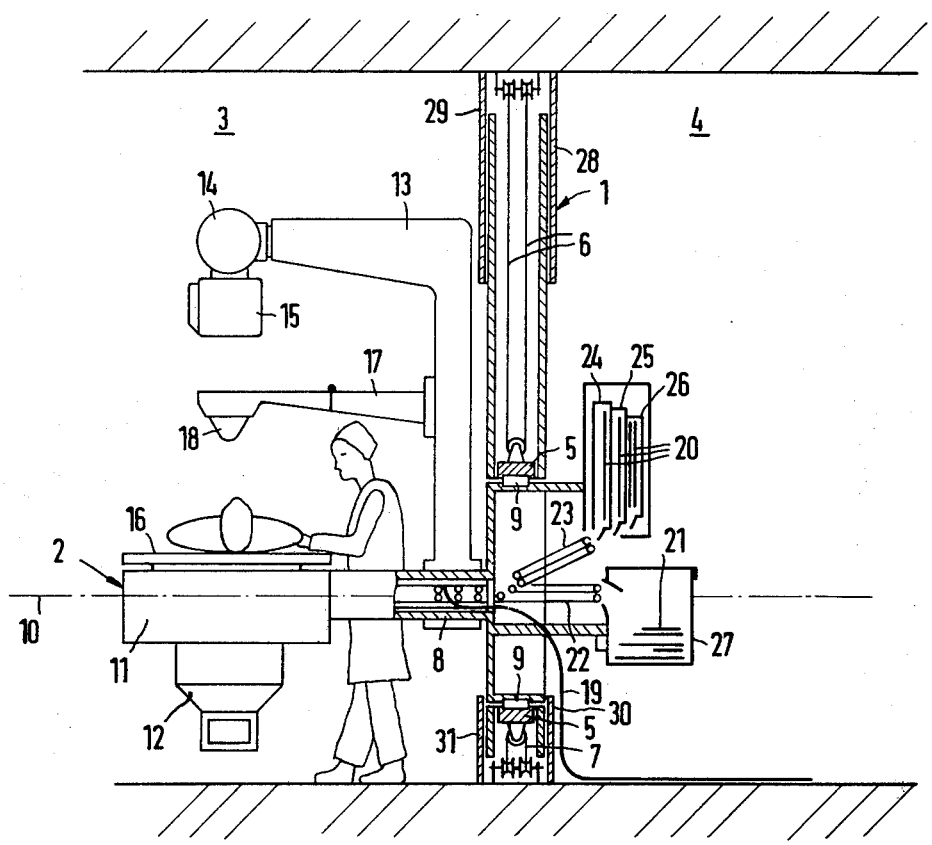
FIG. 1 shows an inventive X-ray examining apparatus in a generally pictorial, partly sectioned elevational view.

Referring now in detail to the drawing, from the sectioned representation in FIG. 1, there may be ascertained a separating wall 1 which divides the room in which the X-ray examining apparatus 2 is located, into an examining room 3 and a work and control room 4. Interiorly of the separating wall there is located a carriage 5 which may, in a motor-driven manner be heightwise moved by means of pulley and tackle 6 and 7. In the carriage 5, a carrier tube 8 is supported through the intermediary of a ball bearing 9 so as to be rotatable about a horizontal axis 10. On the side of the examining room 3, fastened to the carrier tube 8 is an X-ray exposure installation 11 including an image amplifier-video arrangement 12, and an X-ray tube carrier 13 having an X-ray tube 14. The X-ray tube, which is provided with a multileaf collimator 15, is centered relative to the X-ray exposure installation 11. A patient support bed 16 is longitudinally and transversely movably mounted on the housing of the X-ray exposure installation 11. An extension 17 which is movable along the length of the X-ray tube carrier 13 supports a removable compression tube 18 in the path of the beam from the X-ray tube. Interiorly of the carrier tube 8 for the X-ray exposure installation 11, there are located the electrical current supply conduits 19 for the X-ray tube 14 as well as for the X-ray exposure installation 11 with the accompanying image amplifier-video arrangement 12. In addition thereto, the intermediate width of the carrier tube 8 is correlated with the dimensions of the film plates 20, 21 which are to be used and film conveyors 22, 23 are located in the carrier tube by means of which the film plates are transported from the work and control room 4 into the X-ray exposure installation 11, and after exposure, returned from the X-ray exposure installation to the work and control room. Film supply magazines 24, 25, 26 with associated film plate removal arrangements (not shown) for various film types, and a receiving magazine 27 for the exposed film plates, are connected with the film conveyors 22, 23 on the side of the work and control room. Fastened above and below the carriage 5, on both sides thereof, are sheet-metal plates 28, 29, 30 and 31, which are slidingly guided along the separating wall 1. They cover the opening in the separating wall for the carriage in all vertical positions of the carriage. The plates screen the work and control room 4, together with the wall and the carriage, against X-radiation.

Figure 2:
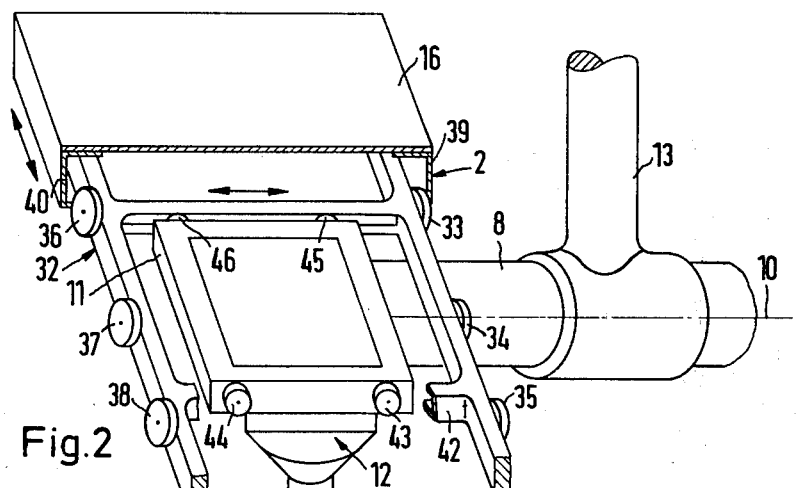
FIG. 2 is a perspective, partly sectioned view of the understructure of the patient's support bed.

In FIG. 2 of the drawings there may be recognized a table frame 32 below the patient support bed 16, which is shown broken open for purposes of illustration. The table frame carries rollers 33, 34, 35, 36, 37, 38 along its two longitudinal edges, on which there are longitudinally displaceably guided the U-shape constructed longitudinal transoms 39, 40 of the patient support bed 16. The table frame has two similarly U-shape constructed cross beams 41, 42 which are on rollers 43, 44, 45, 46 projecting sideways of the X-ray exposure installation 11, so that the patient support bed is also displaceable in a transverse direction. As is readily recognizable in FIG. 3, the X-ray exposure installation 11 is fixedly welded together with the carrier tube 8 so as to form a single unit therewith. The film conveyor 22 extending within the carrier tube 8 consists of two superposed arranged, endless conveyor belts 54, 55 which are guided over rollers 47 to 53, and with the belts being conveyed pressed together on one side thereof. For the purpose of pressing together respectively an end of the two conveyor belts, the conveyor rollers 47 to 53 are in part supported so as to be pressed against each other by means of springs 56, 57 (FIG. 4), or are positioned alternatingly on different sides of the ends of the conveyor belts which are in contact with each other.

Figure 3:
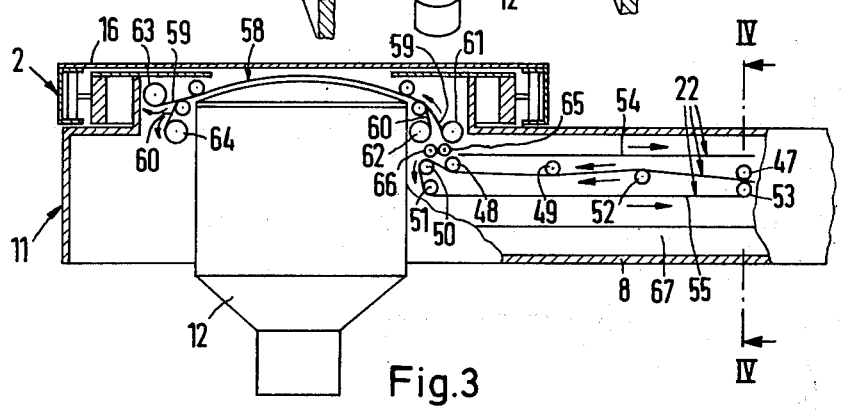
FIG. 3 is a partly sectioned elevational side view of the transport means for the film plates along the carrier tube.
Figure 4:
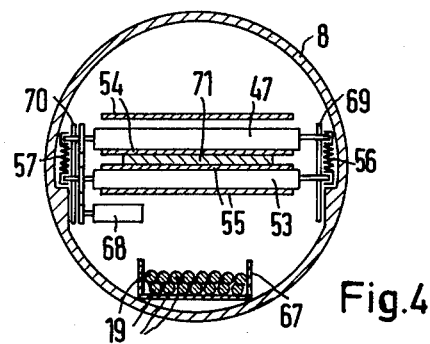
FIG. 4 is a section taken along line IV—IV in FIG. 3, on an enlarged scale.

FIG. 3 also illustrates the manner in which the X-ray image intensifier-video arrangement 12 with its input fluorescent screen is located closely below the patient support bed 16, and the manner in which the film conveyor 58 is conveyed directly above the input fluorescent screen of the lamp intensifier-video arrangement. The film conveyor 58 which pulls the film plates across the input fluorescent screen of the image intensifier-video arrangement, in contradistinction to the remaining film conveyors, consists of two finite transport belts 59, 60 which are superposed and are wound on supply drums 61, 62, 63, 64 at both sides of the image intensifier-video arrangement 12. The oncoming X-ray film plates are threaded between the two supply drums 61, 62 between the finite conveyor belts. Sensors for scanning the film plates are arranged in the film path between the two supply drums 61, 62. In the exemplary embodiment, these sensors consist of resiliently compressed contact rolls 65, 66, between which there are conveyed the film plates. A trough 67 is built into the floor of the carrier tube 8 in which there are placed the electrical cables 19. In a cross-sectional view through the carrier tube, FIG. 4 illustrates the manner in which the conveyor rollers 47, 53 and the drive motor 68 for the conveyor rollers are supported in the sidewise guide plates 69, 70 carried in the carrier tube. They are maintained compressed against each other, and against the film plate conveyed therebetween, through the intermediary of springs 56, 57.

In order to receive a patient 28 who is carried in on a stretcher or litter, the patient support bed 16 is brought into a horizontal position through rotation of the X-ray exposure installation 11 about the horizontal axis 10. By means of the height adjustment of the vertically movable carriage 5 on the separating wall 1, the patient support bed may be lowered to the level of the litter so that the patient can be moved from his litter directly onto the support bed 16. Thereafter, the patient is positioned through the two-dimensional displacement of the patient support bed relative to the X-ray exposure installation 11 and the X-ray tube 14. Hereby, the patient support bed 16 displaces on the rollers 33 to 38 along the table frame 32, and the latter along the U-shaped cross beams 41, 42 on the exposure installation parallel to the horizontal axis 10. The correct positioning of the patient may be easily controlled with the light visor of the multileaf collimator 15. The desired inclination of the patient support bed with respect to the horizontal is achieved through rotation of the carrier tube 8 in carriage 5 about the horizontal axis. Upon approaching one of the two possible vertical positions of the patient support bed 16, due to the height adjustment of carriage 5 there can be avoided an impact between the patient support bed and the floor. All further additional positional changes of the carrier tube may be obviated. Also eliminated are the commonly required guides for the X-ray exposure installation 11 and for the X-ray tube carrier 13, which otherwise always prevented accessability to the patient from the one longitudinal side of the patient support bed. Access to the patient 28 is now afforded from all sides.

Upon the taking of an X-ray exposure, a film plate or sheet having the selected film format is ejected from its respective supply magazine 24 to 26, transported through intermediary of the film conveyor 23 into the film conveyor 22 and, by means of the conveyor belts 54, 55, pushed through the carrier tube 8 between the two supply or feed drums 61, 62. The thereby provided contact rollers 65, 66 are herewith separated by the film sheet 71 passing therethrough. By means of the two conveyor belts 59, 60 which are coiled off from the supply drums, the film sheet is conveyed into the exposure position ahead of the input fluorescent screen of the image intensifier. After the through-passage of the film sheet 71, the drive 68 for the conveyor belts 54, 55, 59, 60 is again deactivated by the again contacting contact rollers after a distance depending upon the selected film format. Subsequent to the taking of the X-ray exposure, the now exposed film sheet is again transported back into the carrier tube 8, and across the film conveyor 22, into the film receiving magazine 27.

Since the hollow-formed X-ray tube carrier 13, the carrier tube 8, and the exposure installation 11 are rigidly interconnected, all electrical conduits 19 may be conducted through the carrier tube 8 into the work and control room 4. This would also be possible, if the X-ray tube carrier 13, for purposes of producing X-ray sectional exposures or angled exposures, were supported on the carrier tube so as to be pivotable toward both sides for an angle of about 30°. In this manner, the examining room 3 is maintained free of supply conduits and cables of all kinds, and thus appears clean and orderly. Since the unexposed film plates 20 are conveyed from one of the film supply magazines 24, 25, 26, which are fastened to the carrier tube 8 in the work and control room, by means of film conveyors 22, 23 through the supply tube 8 into the X-ray exposure installation 11, and back again in the same way to the receiving magazine 27, the examining room 3 need no longer to be entered for effecting the exchange of the film material. Due to the separating wall, the examination of the patient is also functionally separated from the operation of the X-ray examining apparatus 2. When imparting an X-ray protective construction to the separating wall, this will allow for a reduction in the exposure to X-rays of the operating personnel.

While there has been shown what is considered to be the preferred embodiment of the invention, it will be obvious that modifications may be made which come within the scope of the disclosure of the specification.

What is claimed is:

1. An X-ray examining apparatus including an X-ray exposure installation; comprising a tiltable patient support bed; an overhead X-ray tube disposed above said support bed; means supporting said X-ray exposure installation and said X-ray tube for joint rotation about a horizontal axis; said support bed being longitudinally displaceably supported on said X-ray exposure installation; carrier tube means extending along and encompassing said horizontal axis, said X-ray exposure installation being fastened to said carrier tube means; and means for discharging exposed X-ray film material from said X-ray exposure installation through said carrier tube means.

2. An apparatus as claimed in claim 1, comprising a separating wall including X-ray protective screening means forming an examining room, and a work and control room for said X-ray examining apparatus; and vertically slidable carriage means being supported in said separating wall, said carrier tube means being supported on said carriage means for rotation about said horizontal axis.

3. An apparatus as claimed in claim 2, said patient support bed being supported in parallel spaced relationship to said separating wall at a distance in the range of 0.5 to 2.0 meters.

4. An appratus as claimed in claim 1, comprising means for delivering unexposed film material to said X-ray exposure installation through said carrier tube means.

5. An apparatus as claimed in claim 1, comprising film conveying means being located in said carrier tube means.

6. An apparatus as claimed in claim 5, comprising at least one receiving recptacle for exposed film plates being associated with said film conveying means, said receiving receptacle being located at the end of said carrier tube means remote from said X-ray exposure installation.

7. An apparatus as claimed in claim 6, comprising a plurality of film supply receptacles having film plate dispensing arrangements being associated with said film conveying means, said film supply receptacles being located at the end of said carrier tube means remote from said X-ray exposure installation.

* * * * *